United States Patent [19]

Carpentier

[11] 4,159,543

[45] Jul. 3, 1979

[54] HEART VALVE PROSTHESIS

[76] Inventor: Alain Carpentier, 96, rue Didot, 75 - Paris 14ème, France

[21] Appl. No.: 740,879

[22] Filed: Nov. 11, 1976

[30] Foreign Application Priority Data

Nov. 19, 1975 [FR] France .................. 75 36074

[51] Int. Cl.² ............................................. A61F 1/22
[52] U.S. Cl. ...................................... 3/1.5; 137/512.1; 137/527.8
[58] Field of Search .................. 3/1.5; 137/512.1, 527, 137/527.4, 527.8

[56] References Cited

U.S. PATENT DOCUMENTS

| 3,445,863 | 5/1969 | Wada | 3/1.5 |
| 3,546,711 | 12/1970 | Bokros | 3/1.5 |
| 3,825,957 | 7/1974 | Kaster | 3/1.5 |

FOREIGN PATENT DOCUMENTS 1160008  7/1969  United Kingdom .................. 3/1.5

*Primary Examiner*—Ronald L. Frinks
*Attorney, Agent, or Firm*—Stevens, Davis, Miller & Mosher

[57] ABSTRACT

A heart valve is disclosed comprising:
(a) a substantially circular ring having at least one seat and known types of suture means, and
(b) two substantially semicircular movable flaps adapted to rest on the said seat, comprising means permitting the said flaps to undergo movements of rotation through an angle less than 90°, as well as of translation. The flaps can swing, each through an angle of less than 90°, between the said seat and two substantially parallel and transverse shafts serving as stops and limiting the displacements of the said flaps in rotation and in translation. Various refinements and embodiments are disclosed.

3 Claims, 9 Drawing Figures

HEART VALVE PROSTHESIS

The present invention relates to an artificial heart valve for implantation in humans for replacement of damaged heart valves.

It is well known to replace human heart valves by prostheses, which all have a flap device allowing the blood to flow in one direction and preventing it from flowing back in the other. These valves have a plastic ball able to move in a cage (Starr valve) and either freeing or obstructing a metallic seat fixed to the heart; or a disc with parallel displacement in a cage with the same modes as above (Beall valve); or an oscillating disc maintained by two claws (Björk valve).

These prostheses entail the risk of coagulation of the blood, which could block the mechanism of the prosthesis and/or cause embolisms. This risk is principally due to the configuration of these prostheses, which produce turbulence around the occluding ball or disc of the valve.

There is moreover another known mechanism, known as a "butterfly valve", constituted by an elastomeric disc fixed to a central axis (Gott). This disc rests, while the valve is closed, on spikes which are radially disposed and are implanted on the valve body. Because of the existence of a fixed central axis and of spikes which create turbulence, the risks of coagulation are likewise considerable, and therefore this prosthesis has been abandoned.

The object of the present invention is to avoid the disadvantages of the prostheses of the prior art by providing a device that permits flow of blood through the prosthesis, practically without turbulence and without thrombosis. Thus, in accordance with the present invention a heart valve has now been found comprising:

(a) a substantially circular ring having at least one seat and known types of suture means; and
(b) two substantially semicircular movable flaps which can rest on the said seat.

This heart valve is characterized in that it has means permitting the said flaps to move in rotation through an angle less than 90° as well as in translation.

The present invention will be still better understood with the aid of the accompanying drawings which illustrate schematically, and not to scale, various embodiments of the prosthesis merely by way of example:

FIG. 3 is a view from above showing the assembly of the prosthesis according to the variant.

FIGS. 4 and 5 are detail views in partial section along the planes IV and V of FIG. 3.

FIG. 6 is a view of the prosthesis from above and FIG. 7 is a view in partial section showing details.

FIG. 8 is a view from above, and FIG. 9 is a view in partial section showing details.

The cardiac valve according to this invention comprises or consists essentially of two parts: a fixed part and a movable part.

The fixed part is composed of a preferably circular ring 1, for example metallic, the internal face of which is slightly convex. This ring has, for example on its internal face, a slight annular enlargement, the upper face of which, planar and narrow, forms a seat 2 for the flaps 6 and 7. This enlargement can be interrupted at two opposed sections to permit the flaps 6 and 7 to swing. The external surface 3 of the ring is generally hollow, which permits the reception, as suturing means, of for example a flange of fabric (not shown) to fix the valve in place.

Figure 2:
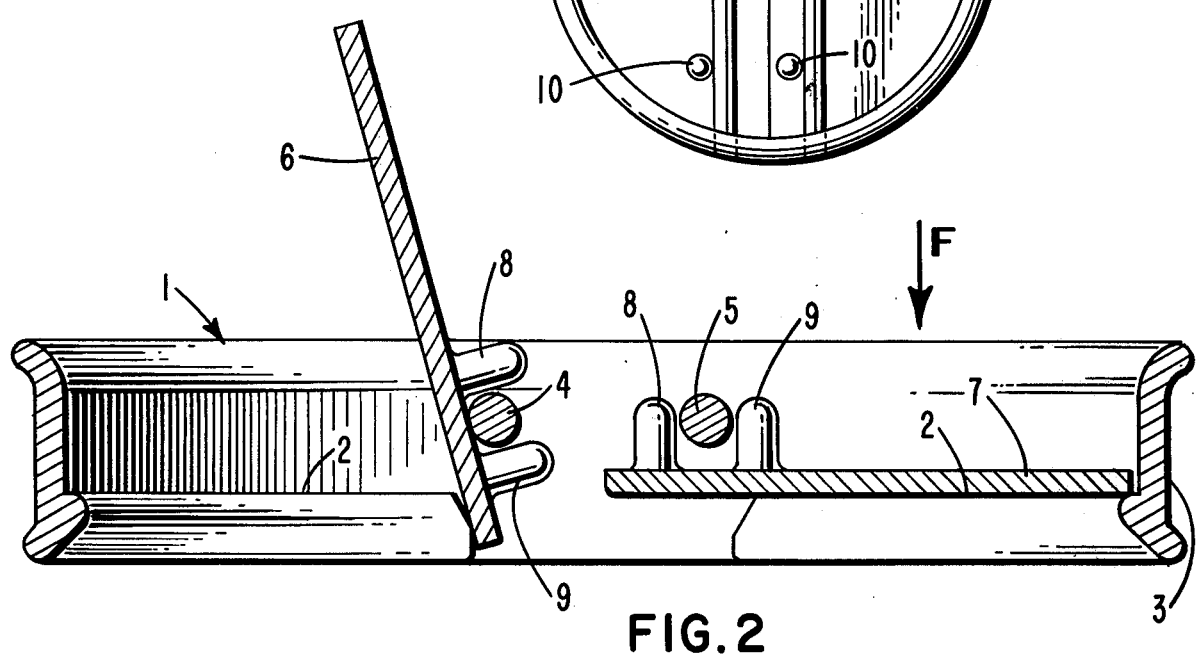
FIG. 2 is a view in section along a diametral plane of the prosthesis shown in FIG. 1. One of the flaps is shown in the closed position, the other in the open position.

There are also shown in FIG. 2, in section, two shafts 4 and 5 constituted by two cylindrical, parallel rods, integral with the ring 1.

The movable parts are constituted by two flaps 6 and 7, preferably semicircular, which are generally flat and thin and are supported by resting on the annular seat 2. These flaps can be provided, on one face, with pegs such as 8, 9 and 10 which frame the rod 5 alternately from one side and from th opposite side.

It will be seen from FIG. 2 that the flaps 6 and 7 can swing between their extreme positions without being in permanent contact with the shafts 4 and 5. They can thus simultaneously undergo a movement of rotation, generally comprised between 60° and 90°, and a movement of translation of several millimeters or tenths of millimeters. Their displacements are limited on the one hand by their seats 2 and on the other hand by the shafts 4 and 5 which act not only like shafts or guides for rotation, but also as stops, while cooperating with the pegs, such as 8, 9 and 10, particularly in the open or closed position of the flaps 6 and 7.

Establishment of permanent local contacts between the fixed parts and the movable parts of the prosthesis is thus avoided, notably in the neighborhood of the shafts. It has been observed that formation of clots is considerably reduced in this way.

It can however be envisaged that it may sometimes be difficult to permit the flaps to be displaced relatively freely between their two extreme positions while simultaneously guiding them such that they always return exactly onto their seat, and such that they never get caught up on or with each other or on the ring, or on the contrary that they are never mutually separated too far in the closed position. It has been found that these difficulties may readily be overcome if the different elements of the prosthesis are selected and arranged in such manner as to permit the flaps to displace in translation, in a direction parallel to the axis of the ring, over distances generally between 0.3 and 4 millimeters.

The valve according to this invention has flaps, no point of which is in permanent contact with the same point of the seat or the shafts; i.e., there is double displacement of each flap.

The operation of the valve according to this invention is as follows:

During opening, two phases can be distinguished:
First Phase: displacement of the flaps parallel to themselves, along the axis of the ring;
Second Phase: from the time when the flaps come into contact with the shaft stops 4 and 5, there is rotation of the flaps around these shafts until the maximum angle of opening is reached.

During closing, the flaps are disengaged from the rotation shafts, permitting washing or flushing of the hinge zones; they then rest on their seat, blocking the orifice.

Advantageously, the flaps open through angles between 70° and 90° relative to the plane of the seat, practically suppressing any turbulence phenomena present in other prostheses in which the opening of the disc is only 60°.

In the open position, there can be distinguished three orifices, of practically equal surface areas and having symmetrical dispositions, ensuring a regular and symmetrical flow.

Figure 1:
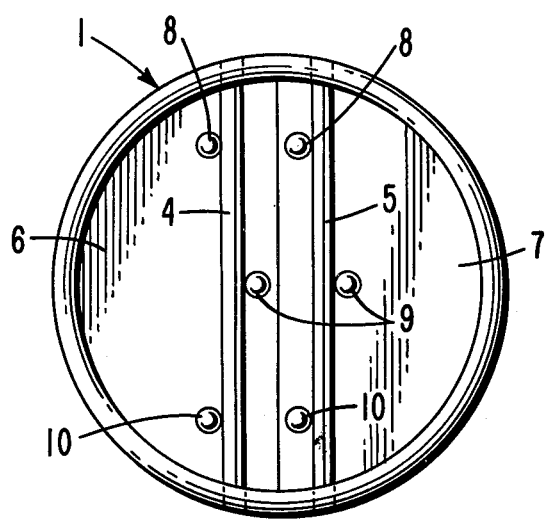
FIG. 1 is a view from above of a first embodiment.
Figure 3:
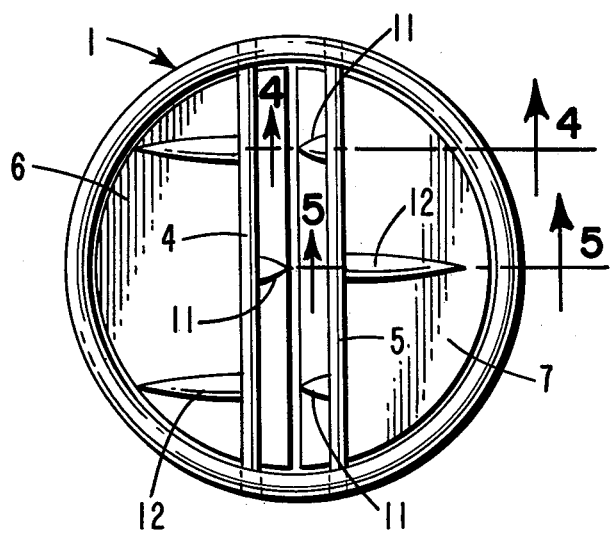
FIGS. 3, 4 and 5 show a variant embodiment of the prosthesis according to FIG. 1.
Figure 4:
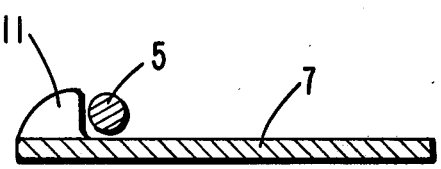
Figure 5:
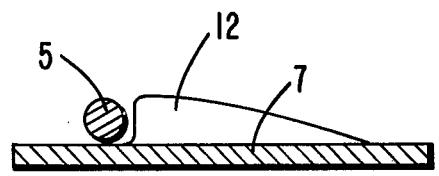

FIGS. 3, 4 and 5 show a variant of the embodiment of the prosthesis shown in FIGS. 1 and 2. In effect, the cylindrical pegs such as 8, 9 and 10 of the first embodiment are advantageously replaced by thin ridges such as 11 and 12, profiled parallel to the direction of blood flow, in order to avoid any turbulence.

Another variant (not shown) is constituted by a prosthesis furnished with an uninterrupted seat within the ring and with flaps which are indented at their bases so that they can swing freely.

Figure 6:
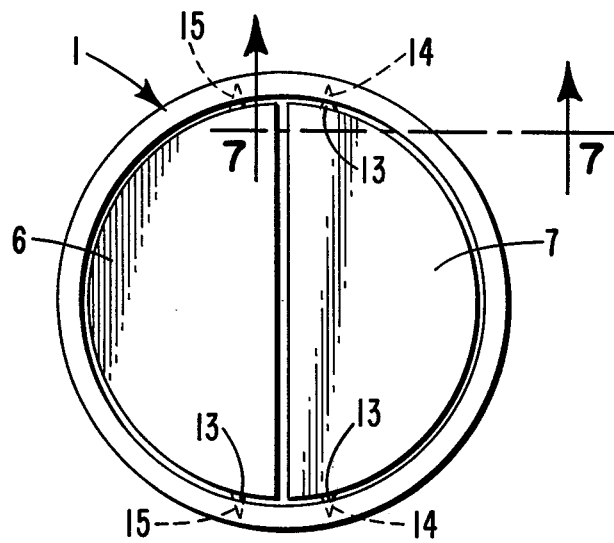
FIGS. 6 and 7 illustrate a second embodiment.
Figure 7:
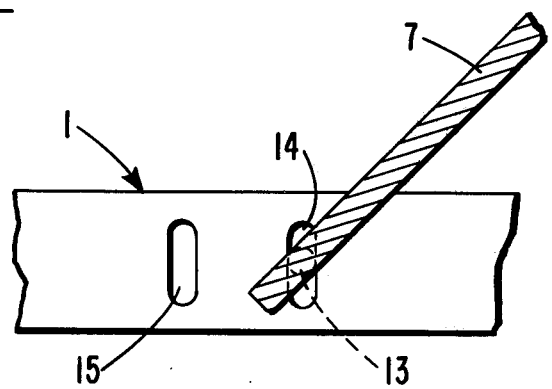

FIGS. 6 and 7 show a second embodiment of the prosthesis according to this invention. Pivots such as 13, for example conical or cylindrical, are integral with the flaps 6 and 7 and can be displaced or move within grooves such as 14 and 15 formed in the ring 1 in a direction parallel to its axis.

Figure 8:
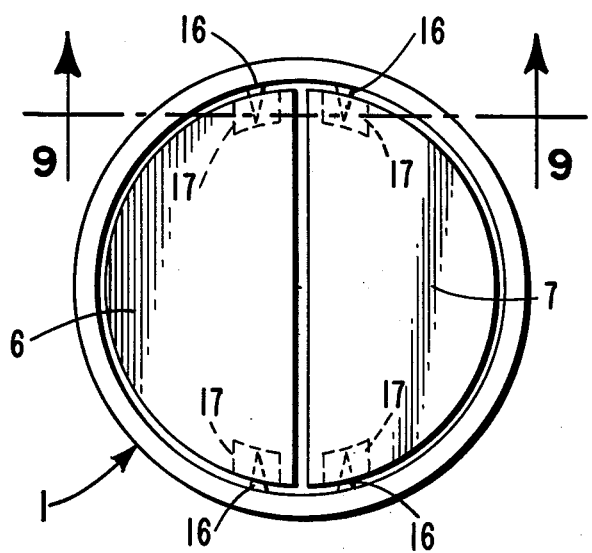
FIGS. 8 and 9 illustrate a third embodiment of the prosthesis.
Figure 9:
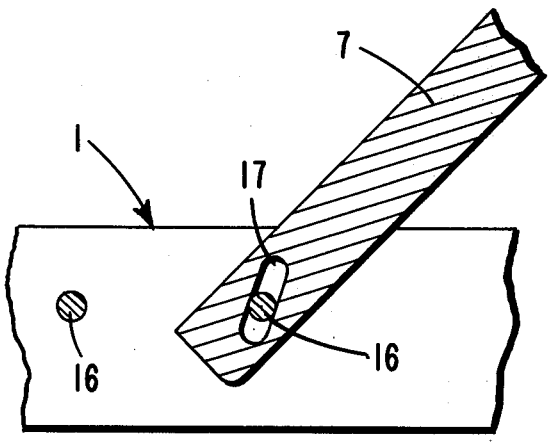

FIGS. 8 and 9 show a third embodiment of the prosthesis according to this invention. Pivots such as 16 are integral with the ring 1, and the flaps 6 and 7 are provided with grooves which are oblique with respect to the plane of the flaps; these grooves can be displaced around the pivots. These pivots 16 perform the function of the shafts 4 and 5 described previously.

Various dispositions and other details, particularly of dimensions, can be made in these valves according to their desired applications, particularly as mitral or aortic valves. Naturally, many variations will occur to those skilled in the art without falling outside the scope of the present invention.

What is claimed is:
1. A heart valve comprising:
 (a) a substantially circular ring having at least one seat and known types of suture means, and
 (b) two substantially semicircular movable flaps adapted to rest on the said seat, comprising means permitting the said flaps to undergo movements of rotation through an angle less than 90°, as well as of translation, the said flaps being adapted to swing, each through an angle of less than 90°, between the said seat and two substantially parallel and transverse shafts serving as stops and limiting the displacements of the said flaps in rotation and in translation, the said shafts being constituted by cylindrical rods which are parallel and each having a fixed position with respect to the ring, the said rods cooperating with pegs disposed on the same face of the said flaps with respect to the said rods.
2. A heart valve according to claim 1, characterized in that the said pegs have the form of profiled ridges.
3. A heart valve comprising:
 (a) a substantially circular ring having at least one seat and known types of suture means, and
 (b) two substantially semicircular movable flaps adapted to rest on the said seat, comprising means permitting the said flaps to undergo movements of rotation through an angle less than 90°, as well as of translation, the said flaps being adapted to swing, each through an angle of less than 90°, between the said seat and two substantially parallel and transverse shafts serving as stops and limiting the displacements of the said flaps in rotation and in translation, said flaps not being in permanent contact with said shafts, the said shafts being constituted by cylindrical parallel rods, each having a fixed position with respect to the ring, the said rods cooperating with pegs disposed on the same face of the said flaps with respect to the said rods.

* * * * *